United States Patent [19]

Markezich

[11] 4,247,448

[45] Jan. 27, 1981

[54] THERMALLY STABLE POLYCARBONATE COMPOSITIONS COMPRISING OXETANE PHOSPHONITES

[75] Inventor: Ronald L. Markezich, Mt. Vernon, Ind.

[73] Assignee: General Electric Company, Pittsfield, Mass.

[21] Appl. No.: 957,426

[22] Filed: Nov. 2, 1978

[51] Int. Cl.³ .................... C07F 9/28; C08K 5/15; C08K 5/50

[52] U.S. Cl. .................... 260/45.8 A; 260/45.7 P; 260/45.7 PH; 260/962; 528/196

[58] Field of Search .................. 260/45.7 P, 333, 962, 260/45.8 A; 528/287 (U.S. only)

[56] References Cited

U.S. PATENT DOCUMENTS

| | | | |
|---|---|---|---|
| 2,274,291 | 2/1942 | Clayton et al. | 260/962 |
| 2,325,076 | 7/1943 | Reuter | 260/967 |
| 2,910,483 | 10/1959 | Schnell et al. | 106/176 |
| 3,050,499 | 8/1962 | Gordon et al. | 260/962 |
| 3,057,904 | 10/1962 | Reetz et al. | 260/962 |
| 3,058,935 | 10/1962 | Starck et al. | 528/287 |
| 3,305,520 | 2/1967 | Fritz et al. | 260/45.7 PH |
| 3,525,711 | 8/1970 | Jenkner | 528/287 |
| 3,794,629 | 2/1974 | Eimers et al. | 260/45.8 A |
| 3,809,676 | 5/1974 | Liberti | 260/45.7 P |
| 3,978,020 | 8/1976 | Liberti | 260/45.7 P |
| 4,073,769 | 2/1978 | Eimers et al. | 260/45.8 A |

FOREIGN PATENT DOCUMENTS 853982  11/1960  United Kingdom .

Primary Examiner—Hosea E. Taylor
Assistant Examiner—R. A. White
Attorney, Agent, or Firm—William F. Mufatti

[57] ABSTRACT

Thermally stable polycarbonate compositions are obtained by admixing with a high molecular weight aromatic polycarbonate resin a stabilizing amount of a phosphonite oxetane.

23 Claims, No Drawings

THERMALLY STABLE POLYCARBONATE COMPOSITIONS COMPRISING OXETANE PHOSPHONITES

This invention relates to thermally stable polycarbonate compositions comprising an admixture of an aromatic polycarbonate and a stabilizing amount of a phosphonite oxetane.

BACKGROUND OF THE INVENTION

In the past, much effort has been expended in preparing thermally stable polycarbonate compositions which would be color stable at elevated temperatures and particularly at the high molding temperatures generally employed to prepare molded polycarbonate articles. Many different additives have been found that are quite suitable for rendering polycarbonates heat and color stable. Particularly useful are triorgano phosphites such as are disclosed in U.S. Pat. No. 3,305,520. In addition, U.S. Pat. Nos. 3,729,440 and 3,953,388 disclose thermally stable aromatic polycarbonates containing a phosphinite and an epoxy compound. Further, U.S. Pat. No. 3,794,629 discloses chemically stable aromatic polycarbonates containing oxetane phosphites and U.S. Pat. No. 3,978,020 discloses thermally stable aromatic polycarbonates containing phosphonites which include epoxy compounds.

Polycarbonates are also used for producing bottles; however, these bottles become hazy after sterilization in water or exposure to moisture at elevated temperatures. U.S. Pat. No. 3,839,247 discloses a water clear polycarbonate composition which can be used to mold bottles wherein the polycarbonate composition contains an aromatic epoxy or an aliphatic epoxy compound as a stabilizer.

DESCRIPTION OF THE INVENTION

It has been discovered that when an aromatic polycarbonate is admixed with a phosphonite oxetane, the resulting polycarbonate composition has improved thermal stability as exemplified by its resistance to yellowing when subjected to high molding temperatures.

The phosphonite oxetanes that can be used in the present invention are represented by the general structure:

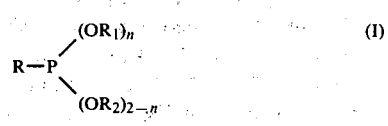

wherein n is 1 or 2; R and $R_2$ can each independently be an alkyl of $C_1$ to $C_{30}$ or an aryl of $C_6$ up to about $C_{30}$, preferably $C_6$–$C_{12}$; and, $R_1$ is an oxetane represented by the structure

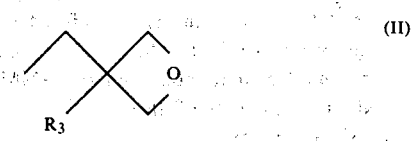

wherein $R_3$ can independently be alkyl, aryl, aralkyl, halomethyl, cyanomethyl, alkoxymethyl, aryloxymethyl, aralkyloxymethyl or acyloxymethyl.

Thus, R and $R_2$ in formula I can independently be unsubstituted and halogen substituted alkyl, aryl, cycloalkyl, aralkyl and alkaryl radicals of about $C_1$–$C_{30}$ so that typical phosphonites that can be employed in the present invention are those wherein R and $R_1$ can be alkyl such as methyl, ethyl, n-propyl, isopropyl, n-butyl, sec-butyl, tertiary butyl, n-amyl, isoamyl, tertiary amyl, n-hexyl, dodecyl, nonyl, and the like; cycloalkyl such as cyclohexyl, 2-methylcyclohexyl, 4-methylcyclohexyl, 2-ethylcyclohexyl, 4-ethylcyclohexyl, 4-isopropylcyclohexyl, and the like; aryl such as phenyl, naphthyl, 2-naphthyl, biphenyl or terphenyl, and the like; aralkyl such as benzyl, phenylethyl, 2-phenylethyl, 1-phenylpropyl, 2-phenylpropyl, and the like; alkaryl such as p-tolyl, m-tolyl, 2,6-xylyl, o-tolyl, p-cumyl, m-cumyl, o-cumyl, mesityl, p-tertiary butylphenyl, and the like; and, haloaryl such as 2-chlorophenyl, 2,4,6-trichlorophenyl, 2,4,6-tribromophenyl, and the like, wherein the substituted portions thereof can be halogen atoms.

The preferred phosphonite oxetanes can be represented by the structure:

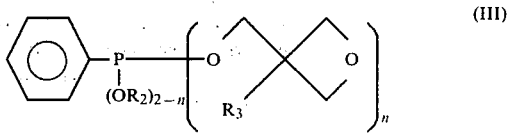

wherein n, $R_2$ and $R_3$ are the same as described above.

The phosphonites of the invention can be prepared by methods known to those skilled in the art such as are described in *Organic Phosphorous Compounds*, Vol. 4, edited by G. M. Kosolapoff and L. Maier (1972), pages 255–462, which is incorporated herein by reference thereto.

Similarly, the oxetanes of the invention can also be prepared by methods known to those skilled in the art such as are described in *Encyclopedia of Polymer Science and Technology*, Interscience Publishers, Vol. 9, pages 668–701 (1968) and in U.S. Pat. No. 2,910,483 and as are referred to and disclosed in U.S. Pat. No. 3,209,013, all of which are incorporated herein by reference.

The phosphonite oxetane is admixed with the aromatic polycarbonate in a stabilizing amount which is generally on the order of about 0.005–1.0, preferably 0.01–0.50 and optimumly about 0.02–0.20 weight percent, based upon the weight of the aromatic polycarbonate.

The aromatic polycarbonate that can be employed in the practice of this invention are homopolymers and copolymers and mixtures thereof that are prepared by reacting a dihydric phenol with a carbonate precursor.

The dihydric phenols that can be employed are bisphenols such as bis(4-hydroxyphenyl)methane, 2,2-bis(4-hydroxyphenyl)propane (bisphenol-A), 2,2-bis(4-hydroxy-3-methylphenyl)propane, 4,4-bis(4-hydroxyphenyl)heptane, 2,2-bis(4-hydroxy-3,5-dichlorophenyl) propane, 2,2-bis(4-hydroxy-3,5-dibromophenyl)propane, etc.; dihydric phenol ethers such as bis(4-hydroxyphenyl)ether, bis(3,5-dichloro-4-hydroxyphenyl)ether, etc.; dihydroxydiphenyls such as p,p'-dihydroxydiphenyl, 3,3'-dichloro-4,4-dihydroxydiphenyl, etc.; dihydroxyaryl sulfones such as bis(4-hydroxyphenyl)sulfone, bis(3,5-dimethyl-4-hydroxyphenyl)sulfone, etc.; dihydroxy benzenes, resorcinol, hydroquinone, halo- and alkyl-substituted dihydroxy benzenes such as 1,4-dihydroxy-2,5-dichlorobenzene, 1,4-dihydroxy-3-methylbenzene, etc.; and dihydroxy diphenyl sulfoxides such as bis(4-hydroxyphenyl)sulfoxide, bis(3,5-dibromo-4-hydroxyphenyl)sulfoxide, etc. A variety of additional dihydric phenols are also available to provide carbonate polymers such as are disclosed in U.S. Pat. Nos. 2,999,835, 3,028,365 and 3,153,008. Also suitable for preparing the aromatic carbonate polymers are copolymers prepared from the above dihydric phenols copolymerized with halogen-containing dihydric phenols such as 2,2-bis(3,5-dichloro-4-hydroxyphenyl)propane, 2,2-bis(3,5-dibromo-4-hydroxyphenyl)propane, etc. It is also possible to employ two or more different dihydric phenols or a copolymer of a dihydric phenol with a glycol or with hydroxy or acid terminated polyester, or with a dibasic acid in the event a carbonate copolymer or interpolymer rather than a homopolymer is desired for use in the preparation of the aromatic polycarbonates of this invention as well as blends of any of the above materials.

The carbonate precursor can be either a carbonyl halide, a carbonate ester or a haloformate. The carbonyl halides which can be employed are carbonyl bromide, carbonyl chloride and mixtures thereof. Typical of the carbonate esters that can be employed are diphenyl carbonate, di-(halophenyl) carbonates such as di-(chlorophenyl) carbonate, di-(bromophenyl) carbonate, di-(trichlorophenyl) carbonate, di-(tribromophenyl) carbonate, etc., di-(alkylphenyl) carbonate such as di-(tolyl) carbonate, etc., di-(naphthyl) carbonate, di-(chloronaphthyl) carbonate, phenyl tolyl carbonate, chlorophenyl chloronaphthyl carbonate, etc., or mixtures thereof. The haloformates suitable for use herein include bishaloformates of dihydric phenols (bischloroformates of hydroquinone, etc.) or glycols (bishaloformates of ethylene glycol, neopentyl glycol, polyethylene glycol, etc.). While other carbonate precursors will occur to those skilled in the art, carbonyl chloride, also known as phosgene, is preferred.

Also included are the polymeric derivatives of a dihydric phenol, a dicarboxylic acid and carbonic acid. These are disclosed in U.S. Pat. No. 3,169,121 which is incorporated herein by reference.

The aromatic polycarbonates of this invention are prepared by employing a molecular weight regulator, an acid acceptor and a catalyst. The molecular weight regulators which can be employed include monohydric phenols such as phenol, chroman-I, paratertiarybutylphenol, parabromophenol, primary and secondary amines, etc. Preferably, phenol is employed as the molecular weight regulator.

A suitable acid acceptor can be either an organic or an inorganic acid acceptor. A suitable organic acid acceptor is a tertiary amine and includes such materials as pyridine, triethylamine, dimethylaniline, tributylamine, etc. The inorganic acid acceptor can be one which can be either a hydroxide, a carbonate, a bicarbonate, or a phosphate of an alkali or alkaline earth metal.

The catalysts which can be employed can be any of the suitable catalysts that aid the polymerization of bisphenol-A with phosgene. Suitable catalysts include tertiary amines such as triethylamine, tripropylamine, N,N-dimethylaniline, quaternary ammonium compounds such as tetraethylammonium bromide, cetyl triethylammonium bromide, tetra-n-heptylammonium iodide, tetra-n-propylammonium bromide, tetramethylammoninum chloride, tetramethylammonium hydroxide, tetra-n-butylammonium iodide, benzyltrimethylammonium chloride and quaternary phosphonium compounds such as n-butyl-triphenyl phosphonium bromide and methyltriphenyl phosphonium bromide.

Also included herein are branched polycarbonates wherein a polyfunctional aromatic compound is reacted with the dihydric phenol and carbonate precursor to provide a thermoplastic randomly branched polycarbonate.

These polyfunctional aromatic compounds contain at least three functional groups which are carboxyl, carboxylic anhydride, haloformyl or mixtures thereof. Examples of these polyfunctional aromatic compounds include trimellitic anhydride, trimellitic acid, trimellityl trichloride, 4-chloroformyl phthalic anhydride, pyromellitic acid, pyromellitic dianhydride, mellitic acid, mellitic anhydride, trimesic acid, benzophenonetetracarboxylic acid, benzophenonetetracarboxylic anhydride, and the like. The preferred polyfunctional aromatic compounds are trimellitic anhydride or trimellitic acid, or their haloformyl derivatives.

Also included herein are blends of a linear polycarbonate and a branched polycarbonate.

Obviously, other materials can also be employed with the aromatic polycarbonates of this invention and include such materials as antistatic agents, mold release agents, ultraviolet light stabilizers, reinforcing fillers such as glass and other inert fillers, foaming agents and the like.

DESCRIPTION OF THE PREFERRED EMBODIMENT

The following examples are set forth to more clearly illustrate the invention. Unless otherwise specified, parts or percents are by weight.

EXAMPLE 1

Method of Preparing A new Phosphonite Oxetane

Bis-[(3-ethyloxytanyl-3)-methyl]benzene phoshponite 127 grams (0.43 mole) of diphenylbenzene phosphonite, 127 grams (1.09 moles) of 3-ethyl-3-hydroxymethyloxetane, and 0.5 grams of sodium methoxide were heated for 2 hours at a temperature from 130° to 160° C. at 15 mm Hg. Phenol was removed from the reaction mixture through a 12" Vigreaux column at a head temperature of 77° to 78° C. at 15 mm Hg. The vacuum was reduced to 0.3 mm Hg to insure complete removal of phenol and excess oxetane. The product, bis-[(3-ethyloxetanyl-3)-methyl]benzene phosphonite, can be recovered by filtering the neat product or by dissolving it in an inert solvent and filtering. Preferably, the product is distilled and in this example, it was distilled at 164° to 165° C. at 0.3 mm Hg to afford a clear colorless liquid. When subjected to infrared spectrum (IR) and proton nuclear magnetic resonance (NMR) analysis, the product revealed the following data and had the structure shown below:

IR: peaks at 2957, 2925, 2865, 1241 and 1000 cm$^{-1}$.

NMR: 5 aromatic protons centered at 7.5$\delta$; 12 protons centered at 4.2$\delta$; and, 10 aliphatic protons centered at 1.8 and 0.8$\delta$.

Structure:

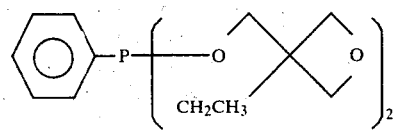

EXAMPLE 2

Alternate Method of Preparing Phosphonite Oxetane of Example 1

To a round-bottom flask containing 58.1 grams (0.5 mole) of 3-ethyl-3-hydroxymethyloxetane, 51.0 grams (0.5 mole) of triethylamine, and 250 ml of dichloromethane was added dropwise, while stirring 44.8 grams (0.25 mole) of dichlorophenylphosphine. After the addition, the mixture was stirred for an additional 60 minutes and then filtered to remove triethylamine hydrochloride. To the dichloromethane solution was added an equal volume of diethylether and the mixture filtered again. The solvent was removed in vacuo and an additional 100 ml of diethylether added and the mixture refiltered. Removal of the solvent in vacuo and drying at 0.4 mm Hg overnight afforded bis-[(3-ethyloxetanyl-3)-methyl]-benzene phosphonite.

EXAMPLE 3

Method of Preparing A New Phosphonite Oxetane

Phenyl-[(3-ethyloxytanyl-3)-methyl]benzene phosphonite 147.1 grams (0.5 mole) of diphenylbenzene phosphonite, 58.1 grams (0.5 mole) of 3-ethyl-3-hydroxymethyloxetane, and 0.5 gram of sodium methoxide were heated for 4 hours at a temperature from 100° to 160° C. at 14 mm Hg. Phenol was removed from the reaction mixture through a 12" Vigreaux column at a head temperature of 75° to 77° C. at 14 mm Hg. The vacuum was reduced to 0.4 mm Hg to insure complete removal of phenol and any oxetane alcohol. The product, phenol-[(3-ethyloxetanyl-3)-methyl]benzene phosphonite, remaining in the reaction vessel was distilled at 158° to 159° C. at 9.4 mm Hg to afford a clear colorless liquid. IR and NMR analysis of the product revealed the following data and it had the structure shown below:

IR: peaks at 3055, 2960, 2930, 2865, 1591, 1490, 1216 and 1000 cm$^{-1}$.

NMR: 10 aromatic protons centered at 7.4δ; 6 protons centered at 4.2δ; and, 5 aliphatic protons centered at 1.8 and 0.8δ.

Structure:

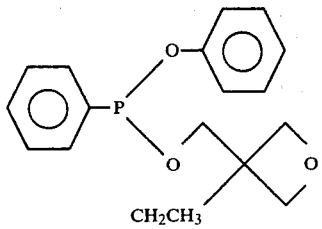

EXAMPLE 4

A polycarbonate composition of a homopolymer of 2,2-bis(4-hydroxyphenyl)propane (bisphenol-A) was prepared by reacting essentially equimolar amounts of bisphenol-A and phosgene in an organic medium with triethylamine, sodium hydroxide and phenol under standard conditions and was mixed with the stabilizers shown in Table I by tumbling the ingredients in a laboratory tumbler. This mixture was then fed to an extruder, which extruder was operated at about 500° F., and the extruded strands chopped into pellets. The pellets were then injected molded at 600° F. and 680° F. into test samples of about 3 inches by 2 inches by ⅛ inch thick. Thermal stability to discoloration of the test samples was measured in accordance with ASTM Yellowness Index (YI) Test D1925 on samples molded at 600° F. and 680° F. The results obtained are set forth in Table I below wherein "Control" identifies the polycarbonate without stabilizer.

TABLE I

| | | Thermal Stability | |
|---|---|---|---|
| | Amount | YI of Test Samples Molded At: | |
| Stabilizer | (wt %) | 600° F. | 680° F. |
| Control | — | 7.2 | 16.0 |
| *A | 0.1 | 4.4 | 10.2 |
| **B | 0.04 | 4.8 | 6.3 |
| B | 0.1 | 3.8 | 5.9 |
| Example 2 | 0.04 | 4.8 | 7.6 |
| Example 2 | 0.1 | 4.0 | 14.1 |

*As disclosed in Ger. Pat. 1,694,285 and referred to in U.S. Pat. No. 3,794,629: 1 part octyldiphenyl phosphite 2 parts 3,4-epoxy-cyclohexylmethyl-3,4-epoxycyclohexane carboxylate
**As disclosed in U.S. Pat. No. 3,794,629: tris-[(3-ethyloxetanyl-3)-methyl]phosphite

EXAMPLE 5

The molded test samples of Example 4 were also subjected to ASTM D1003 to measure their light transmission before and after they were steam autoclaved at 250° F. to determine their hydrolytic stability. The results obtained are shown in Table II below.

Table II

| | Hydrolytic Stability | | | |
|---|---|---|---|---|
| | | % Light Transmission Stabilizer (wt %) | | |
| Time (hrs) | Control | A(0.1) | B(0.04) | Example 2(0.004) |
| 0 | 89.2 | 90.3 | 90.0 | 90.0 |
| 24 | 88.5 | 86.0 | 89.8 | 89.6 |
| 48 | 87.9 | 74.5 | 89.1 | 88.9 |
| 72 | 88.0 | 41.3 | 88.6 | 88.9 |
| 96 | 87.5 | 17.4 | 87.6 | 88.2 |
| 120 | 87.5 | — | 85.3 | 87.3 |
| 144 | 86.4 | — | 78.0 | 86.3 |
| 168 | 84.7 | — | 42.6 | 84.9 |
| 192 | 86.9 | — | 45.8 | 86.3 |

The results in Table I above show the effect of the stabilizers on color stability when the stabilizers are employed at different concentrations. Significantly, the results of Table II reveal that the Example 2 stabilizer retains the hydrolytic stability of the polycarbonate over prolonged periods of time whereas stabilizer A fails at 48 hours and stabilizer B fails at 144 hours, the failure level being typically acknowledged when the light transmission level is less than about 75%.

EXAMPLE 6

A polycarbonate composition was prepared as described in Example 4 except that a trace amount of a commercially obtained organic blue pigment was added. The polycarbonate composition was then admixed with stabilizers, extruded, and molded into test samples and the YI of the test samples was determined as described in Example 4. In addition, the test samples molded at 680° F. were subjected to accelerated heat aging by placing them in an oven which was maintained at a temperature of 140° C. for a period of one week and two weeks. The results obtained are shown in Table III below.

Table III

| Stabi-lizer | A-mount (wt %) | YI of Test Samples Molded At | | YI of Heat Aged 680° F. Molded Test Samples After | |
|---|---|---|---|---|---|
| | | 600° F. | 680° F. | 1 week | 2 weeks |
| A | 0.1 | 2.8 | 6.7 | 17.3 | 23.0 |
| B | 0.1 | 1.8 | 3.9 | 8.7 | 13.4 |
| Ex. 1 | 0.04 | 2.1 | 4.0 | 8.6 | 12.5 |
| Ex. 1 | 0.08 | 2.0 | 3.4 | 7.6 | 12.2 |

As the results in Table III above reveal, stabilizer B and the Example 1 stabilizer are both better than stabilizer A for test samples molded at 600° F. and 680° F. However, upon being heat aged, the Example 1 stabilizer shows a significant improvement over both the A and B stabilizers, particularly after being heat aged for two weeks, and this improvement is obtained at substantially lower Example 1 concentrations.

EXAMPLE 7

The YI of test samples containing stabilizer A and test samples containing the stabilizers of Example 1 and Example 3 were again determined and the results obtained are set forth in Table IV below.

Table IV

| Stabilizer | Amount (wt %) | YI of Test Samples Molded At | |
|---|---|---|---|
| | | 600° F. | 680° F. |
| Control | — | 3.4 | 5.3 |
| A | 0.1 | 2.0 | 8.0 |
| Ex. 1 | 0.04 | 2.1 | 3.7 |
| Ex. 1 | 0.08 | 1.7 | 3.9 |
| Ex. 3 | 0.04 | 2.0 | 4.1 |
| Ex. 3 | 0.08 | 1.7 | 3.8 |

The results in Table IV reveal the improved YI results for the stabilizers of Example 1 and Example 3 even though employed at substantially lower concentrations than stabilizer A and particularly for samples molded at the higher temperature of 680° F.

EXAMPLE 8

The hydrolytic stability of test samples containing stabilizers A and B and those containing the stabilizers of Example 1 and Example 3 were again determined and the results obtained are set forth in Table V below.

Table V

| | Hydrolytic Stability | | | |
|---|---|---|---|---|
| | % Light Transmission/Stabilizer (wt %) | | | |
| Time (hrs.) | A(0.1) | B(0.08) | EX. 1(0.08) | Ex. 3(0.08) |
| 0 | 87.4 | 87.5 | 87.6 | 87.6 |
| 24 | 84.4 | 71.4 | 86.4 | 86.2 |
| 48 | 19.1 | 9.8 | 82.6 | 62.5 |
| 72 | — | — | 85.3 | 67.8 |

The results in Table V above reveal that stabilizer A failed before 48 hours, stabilizer B failed in 24 hours, the stabilizer of Example 1 was still acceptable after 72 hours and although the stabilizer of Example 3 failed before 48 hours, it was still better than either stabilizer A and stabilizer B after 24 hours.

Although the stabilizers of the invention have been particularly shown employed with high molecular weight aromatic polycarbonates, it should be understood that this has been by way of illustrating the general efficacy of these stabilizers with thermoplastic resins. As will be apparent to the skilled artisan, the stabilizers of the invention can also be employed with other thermoplastics such as polyolefins, polyvinyl chloride, polyesters and the like, with substantially similar facility and efficacy.

What is claimed is:

1. A phosphonite oxetane compound represented by the structure:

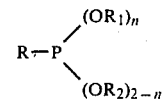

wherein n is 1 or 2; R and $R_2$ can each independently be an alkyl of about $C_1-C_{30}$ or an aryl of about $C_6-C_{30}$; and $R_1$ is an oxetane represented by the structure:

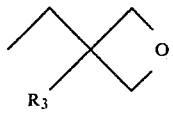

wherein $R_3$ can independently be an alkyl, aryl, aralkyl, halomethyl, cyanomethyl, alkoxymethyl, aryloxymethyl, aralkyloxymethyl, or acyloxymethyl.

2. The phosphonite oxetane compound of claim 1 wherein said aryl of said R and $R_2$ is one having about $C_6-C_{12}$.

3. A phosphonite oxetane compound represented by the structure:

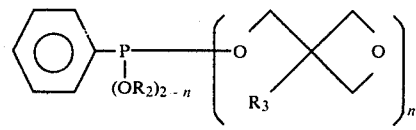

wherein n is 1 or 2; $R_2$ can independently be an alkyl of about $C_1-C_{30}$ or an aryl of about $C_6-C_{30}$; and $R_3$ can independently be an alkyl, aryl, aralkyl, halomethyl, cyanomethyl, alkoxymethyl, aryloxymethyl, aralkyloxymethyl, or acyloxymethyl.

4. The phosphonite oxetane compound of claim 3 wherein said aryl of said R and $R_2$ is one having about $C_6-C_{12}$.

5. A phosphonite oxetane compound having the structure:

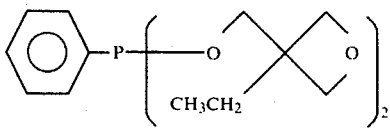

6. A phosphonite oxetane compound having the structure

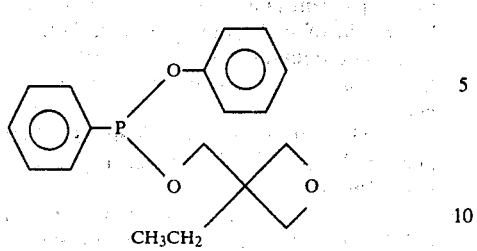

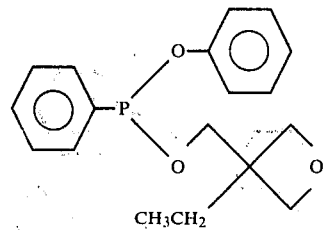

7. A thermally and hydrolytically stabilized thermoplastic composition comprising an admixture of a thermoplastic resin polymer selected from the group consisting of aromatic polycarbonates, polyolefins, polyvinyl chlorides and polyesters, and a stabilizing amount of a phosphonite oxetane stabilizer represented by the structure:

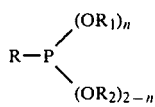

wherein n is 1 or 2; R and $R_2$ can each independently be an alkyl of about $C_1$–$C_{30}$ or an aryl of about $C_6$–$C_{30}$; and $R_1$ is an oxetane represented by the structure:

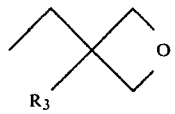

wherein $R_3$ can independently be an alkyl, aryl, aralkyl, halomethyl, cyanomethyl, alkoxymethyl, aryloxymethyl, aralkyloxymethyl, or acyloxymethyl.

8. The composition of claim 7 wherein said stabilizer is represented by the structure

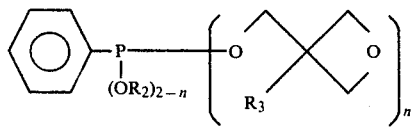

9. The composition of claim 8 wherein said aryl of said $R_2$ is one having about $C_6$–$C_{12}$.

10. The composition of claim 7 wherein said stabilizer has the structure

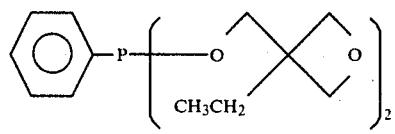

11. The composition of claim 7 wherein said stabilizer has the structure

12. The composition of claim 7 wherein said stabilizer is present in an amount of about 0.005–1.0 percent by weight of said thermoplastic resin.

13. The composition of claim 12 wherein said stabilizer is present in an amount of about 0.01–0.50 weight percent.

14. A thermally and hydrolytically stabilized aromatic polycarbonate composition comprising an admixture of a high molecular weight aromatic polycarbonate and a stabilizing amount of a phosphonite oxetane stabilizer represented by the structure $$R-P\begin{matrix}(OR_1)_n\\(OR_2)_{2-n}\end{matrix}$$

wherein n is 1 or 2; R and $R_2$ can each independently be an alkyl of about $C_1$–$C_{30}$ or an aryl of about $C_6$–$C_{30}$; and $R_1$ is an oxetane represented by the structure wherein $R_3$ can independently be an alkyl, aryl, aralkyl, halomethyl, cyanomethyl, alkoxymethyl, aryloxymethyl, aralkyloxymethyl, or acyloxymethyl.

15. The composition of claim 14 wherein said stabilizer is represented by the structure

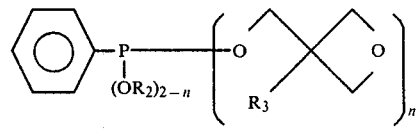

16. The composition of claim 15 wherein said aryl of said $R_2$ is one having about $C_6$–$C_{12}$.

17. The composition of claim 14 wherein said stabilizer has the structure

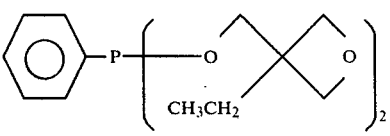

18. The composition of claim 14 wherein said stabilizer has the structure

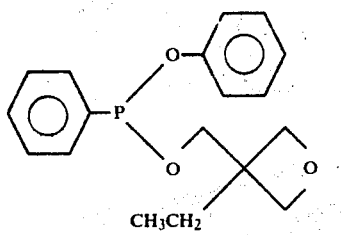

19. The composition of claim 14 wherein said stabilizer is present in an amount of about 0.005–1.0 percent by weight of said aromatic polycarbonate.

20. The composition of claim 19 wherein said stabilizer is present in an amount of about 0.01–0.50 weight percent.

21. The composition of claim 14 wherein said aromatic polycarbonate is derived from 2,2-bis(4-hydroxyphenyl)propane.

22. The composition of claim 7 which includes a stabilizing amount of an epoxide co-stabilizer.

23. The composition of claim 14 which includes a stabilizing amount of an epoxide co-stabilizer.

* * * * *